United States Patent [19]
Regan et al.

[11] Patent Number: 5,688,797
[45] Date of Patent: Nov. 18, 1997

[54] TREATMENT OF ACUTE CENTRAL NERVOUS SYSTEM INJURY WITH PIPERAZINE DERIVATIVES

[75] Inventors: Raymond F. Regan, Villanova; Edward H. Jasper, Ottsville, both of Pa.

[73] Assignee: Thomas Jefferson University, Philadelphia, Pa.

[21] Appl. No.: 639,908

[22] Filed: Apr. 26, 1996

[51] Int. Cl.$^6$ ............................................. A61K 31/495
[52] U.S. Cl. ............................................. 514/255
[58] Field of Search ............................................. 514/255

[56] References Cited

U.S. PATENT DOCUMENTS

| | | | |
|---|---|---|---|
| 3,941,790 | 3/1976 | Creighton | 260/268 DK |
| 4,755,619 | 7/1988 | Creighton et al. | 560/169 |
| 4,764,614 | 8/1988 | Miller | 544/357 |
| 4,902,714 | 2/1990 | Creighton et al. | 514/459 |
| 4,943,578 | 7/1990 | Naylor et al. | 514/252 |
| 4,963,551 | 10/1990 | Palepu et al. | 514/252 |
| 4,973,685 | 11/1990 | Schmidt et al. | 540/227 |
| 5,149,710 | 9/1992 | Creighton et al. | 514/547 |
| 5,162,372 | 11/1992 | Creighton et al. | 514/547 |
| 5,242,901 | 9/1993 | Speyer et al. | 514/8 |
| 5,278,187 | 1/1994 | Creighton et al. | 514/459 |
| 5,492,913 | 2/1996 | Wierzbicki et al. | 514/255 |

OTHER PUBLICATIONS

Gwag, B. et al., "BDNF or IGF-I Potentiates Free radical-Mediated Injury in Cortical Cell Cultures", *NeuroReport* 1995, 7, 93-96.

Koh, J.-Y. et al., "Potentiated Necrosis of Cultured Cortical neurons by Neurotrophins", *Science* 1995, 268, 573-575.

"The Merck Index", No. 8026, p. 8020. (1985).

*Primary Examiner*—Raymond Henley, III
*Attorney, Agent, or Firm*—Woodcock Washburn Kurtz Mackiewicz & Norris LLP

[57] ABSTRACT

A method of treating patients suffering from acute trauma of the central nervous system is described. The method comprises identifying such patient and administering one or more piperazine derivative or mixtures thereof to said patient.

5 Claims, 1 Drawing Sheet

DEXRAZOXANE ATTENUATES BDNF NEUROTOXICITY

DEXRAZOXANE ATTENUATES HEMOGLOBIN NEUROTOXICITY

TREATMENT OF ACUTE CENTRAL NERVOUS SYSTEM INJURY WITH PIPERAZINE DERIVATIVES

FIELD OF THE INVENTION

This invention relates to the treatment of acute central nervous system injury. More particularly, the invention relates to treatment of acute central nervous system injury by administration of a piperazine derivatives.

OBJECTS OF THE INVENTION

It is an object of the present invention to provide a method of treating acute central nervous system injury.

BACKGROUND OF THE INVENTION

Treatments for many central nervous system (CNS) injuries, conditions and disorders are unsatisfactory. The lack of effective therapies often leads to permanent damage, and sometimes death.

Cerebrovascular diseases are a common cause of neurological disability and sometimes death. Treatment of focal ischemic conditions with anticoagulants and platelet inhibitors may be undertaken in some cases but the patient may not benefit. In addition, after circulation is restored, postischemic lipoperoxidation of the damaged tissue may result in additional neuron damage due to the potentiation of free radicals. Traditional regimes do not prevent such injury.

Trauma head and spinal injuries are leading causes of neurologic disabilities and deaths in many age categories. Treatment, however, is generally limited to ensuring that the patient does not suffocate or bleed to death. Steroids, anticonvulsants and osmotic diuretics are often administered. While these critical procedures are important in addressing the immediate life-threatening hemorrhaging and other cellular damage that accompany such injuries, these conventional treatments do not treat cellular injury caused by neurotoxicity to hemoglobin or other factors such as brain neurotrophic factor.

CNS infections result in inflammation of the brain and spinal cord. Treatment is generally directed at the underlying infection with antibiotics, antiviral compounds, antifungal compounds and/or steroids.

There is a need for improved treatments of CNS injuries, conditions and disorders including treatments which can prevent and/or inhibit the debilitating neurological effects of CNS injuries, conditions and disorders.

SUMMARY OF THE INVENTION

In accordance with certain aspects of the present invention methods of treating acute central nervous system injury in a human are provided comprising identifying a patient suffering from an acute trauma of the CNS and administering an effective amount of one or more piperazine derivatives to the patient. In more preferred embodiments one or more bisdioxopiperazines are administered to a patient. In still more preferred embodiments of the present invention at least one of the piperazines is (+)-1,2-bis(3,5-dioxopiperazinyl-1-yl)propane.

DETAILED DESCRIPTION OF THE PRESENT INVENTION

Figure 1:
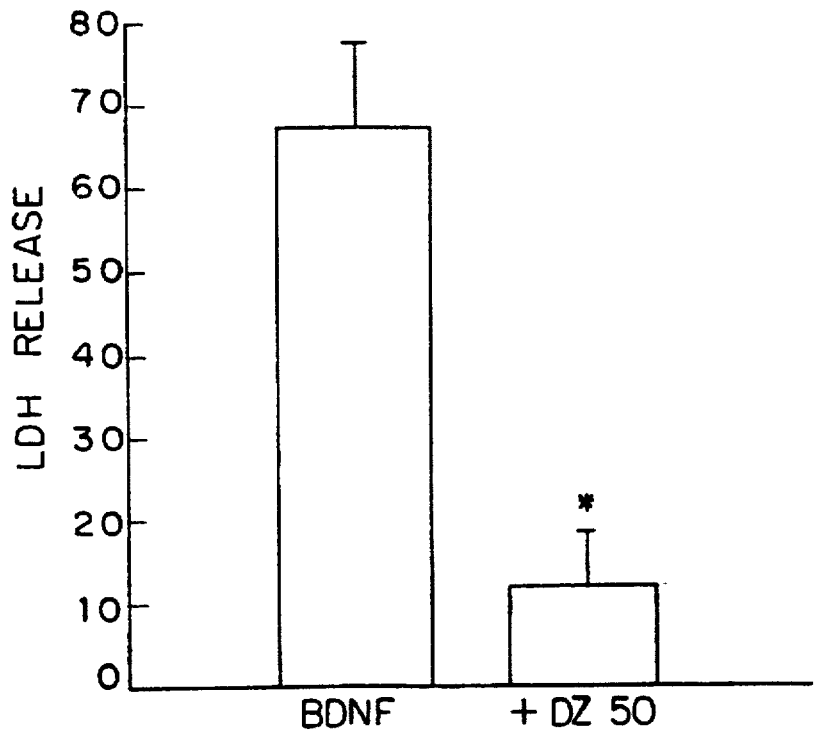
FIG. 1 is a chart showing attenuation of brain derived neurotrophic factor (BDNF) neurotoxicity resulting from treatment with 50 μM of Dexrazoxane (DZ).

As used herein the term "acute central nervous system injury" is meant to refer to CNS injuries, conditions and disorders. Many CNS injuries, conditions and disorders are associated with free radical injury of the neurons. Such CNS injuries, conditions and disorders can be treated by the methods of the invention. CNS injuries, conditions and disorders include cerebrovascular diseases, trauma of the head and spine and CNS infections. Those of ordinary skill in the art can identify those patients suffering from such injuries, conditions and disorders generally by routine examination or diagnosis using CT scan, MRI or other noninvasive imaging techniques.

Examples of cerebrovascular diseases include cerebral insufficiency, infarction, hemorrhage and arteriovenous malformation. Stroke is the term commonly used to refer to ischemic syndromes. Ischemic conditions include atheromas including extracranial atheromas and those caused by intracranial thrombosis, cerebral emboli and physiologic circulatory insufficiency. Focal ischemias such as transient ischemia attacks, stroke in evolution, and completed stroke and global ischemia caused by cardiac arrest are caused by insufficient cerebral circulation. Hemorrhagic syndromes include intracerebral hemorrhage, subarachnoid hemorrhage and intraparachymal hemorrhage. Hemorrhagic syndromes are cerebrovascular disorders caused by bleeding into the brain tissue. Arteriovenous malformations are congenital conditions.

Examples of head injuries include penetrating and blunt head injuries causing cerebral contusions and lacerations, acute subdural or intracerebral hematomas, epidural hematomas, and chronic subdural hematomas. Spinal cord injuries may be caused by lacerations or hemorrhage.

Examples include acute bacterial meningitis, acute viral encephalitis and aseptic meningitis, and subacute and chronic meningitis.

Acute nervous system injuries such as those describe above are often accompanied by hemorrhaging. During hemorrhaging, iron may be released from the hemoglobin resulting in neurotoxicity of neurons. It is hypothesized that the iron released from the hemoglobin results in intracellular iron potentiation of free radical induced injury. In addition, even when acute nervous system injuries are not accompanied by hemorrhaging, other factors may cause neurotoxic affects. For instance, it has recently been reported that brain derived neurotrophic factor (BDNF) produced as a result of acute central nervous system injuries may potentiate free radical injury. *Science*, 1995, 268:573; *Neuroreport*, 1995, 7:93–96.

While some chelators, such as deferoxamine, have been shown to have some effect in treating iron poisoning, hemolytic overload, hemocromatosis, and other iron overload states, these chelators work extracellularly and do not penetrate the central nervous system. Consequently these chelators have not been found to be effective for the treatment of acute central nervous system injuries.

In contrast, compounds of the present invention bind intracellular iron after they hydrolyze in vivo, thereby providing a significant advantage over other chelators.

According to preferred embodiments of the present invention piperazine derivatives can be used to treat CNS injuries, diseases and disorders. Preferred piperazine derivatives, including disclosure of their synthesis, are described in U.S. Pat. No. 3,941,790 issued in 1976 to Creighton, which is incorporated herein by reference. U.S. Pat. No. 4,755,619 issued Jul. 5, 1988 to Creighton, U.S. Pat. No. 4,902,714 issued Feb. 29, 1990 to Creighton, U.S. Pat. No. 5,149,710 issued Sep. 22, 1992 to Creighton, U.S. Pat. No. 5,162,372 issued Nov. 10, 1992 to Creighton, and U.S. Pat. No. 5,278,187 issued Jan. 11, 1994 to Creighton, which are each incorporated herein by reference, describe methods of making and using prodrugs including those of piperazine derivatives which are contemplated to be used in some embodiments of the present invention. Compounds may be synthesized and formulated according to the disclosures in U.S. Pat. No. 4,764,614 issued Aug. 16, 1988 to Miller, and U.S. Pat. No. 4,963,551 issued Oct. 16, 1990 to Tu et al., which are each incorporated herein by reference. In some preferred embodiments bisdioxopiperazine can be used for the treatment of CNS injury. In still more preferred embodiments of the present invention (+)-1,2-bis(3,5-dioxopiperazinyl-1-yl)propane is used in methods of the present invention (+)-1,2-bis(3,5-dioxopiperazinyl-1-yl)propane has the chemical structure

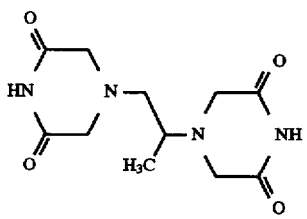

Treatment of CNS injuries, conditions and disorders can be performed by administration of effective amounts of a pharmaceutical preparation of piperazine derivatives. Compounds can be formulated for human therapeutic applications by those having ordinary skill in the art. The dosage range of a compound to be administered to mammals, particularly humans: to be effective in the treatment of CNS injuries, conditions and disorders can be determined by those having ordinary skill in the art.

Pharmaceutical preparations incorporating one or more compounds of the present invention are used in the method that is the invention. The method that is the invention relates to treatment of CNS injuries, conditions and disorders by administration of effective amounts of pharmaceutical preparation that comprise piperazine derivatives disclosed herein. The compounds used in the method that is the invention can be formulated for human therapeutic applications by those having ordinary skill in the art.

The mode of administration of compounds and pharmaceutical compositions according to the method that is the invention includes any means that produces contact of the active ingredient with the agent's site of action in the body of a mammal or in a body fluid or tissue. These modes of administration include but not limited to oral, topical, hypodermal, intravenous, intramuscular and intraparenteral methods of administration. In practicing the method that is the invention, the compounds may be administered singly or in combination with other compounds used in the method that is the invention, other pharmaceutical compounds such as chemotherapeutic compounds, or in conjunction with therapies such as radiation treatment. In the method that is the invention, the compounds are preferably administered with a pharmaceutically acceptable carrier selected on the basis of the selected route of administration and standard pharmaceutical practice.

The method may include administration of compounds to mammals, preferably humans, in therapeutically effective amounts. The dosage administered in any particular instance will depend upon factors such as the pharmacodynamic characteristics of the compound of the invention, its mode and route of administration; age, health, and weight of the recipient; nature and extent of symptoms; kind of concurrent treatment, frequency of treatment, and the effect desired.

It is contemplated that the daily dosage of a compound used in the method that is the invention will be in the range of from about 1 µg to about 100 mg per kg of body weight, preferably from about 1 µg to about 40 mg per kg body weight, more preferably from about 10 µg to about 20 mg per kg per day, and most preferably 10 µg to about 1 mg per kg per day. Pharmaceutical compositions may be administered in a single dosage, divided dosages or in sustained release. Persons of ordinary skill will be able to determine dosage forms and amounts with only routine experimentation based upon the considerations of this invention. Isomers of the compounds and pharmaceutical compositions, particularly optically active stereoisomers, are also within the scope of the present invention.

The method of administering compounds include administration as a pharmaceutical composition orally in solid dosage forms, such as capsules, tablets, and powders, or in liquid dosage forms, such as elixirs, syrups, and suspensions. The compounds may also be administered parenterally in sterile liquid dosage forms or topically in a carrier. The compounds may be formulated into dosage forms according to standard practices in the field of pharmaceutical preparations. See *Remington's Pharmaceutical Sciences*, A. Osol, Mack Publishing Company, Easton, Pa.

Compounds may be mixed with powdered carriers, such as lactose, sucrose, mannitol, starch, cellulose derivatives, magnesium stearate, and stearic acid for insertion into gelatin capsules, or for forming into tablets. Both tablets and capsules may be manufactured as sustained release products for continuous release of medication over a period of hours. Compressed tablets can be sugar or film coated to mask any unpleasant taste and protect the tablet from the atmosphere or enteric coated for selective disintegration in the gastrointestinal tract.

Liquid dosage forms for oral administration may contain coloring and flavoring to increase patient acceptance, in addition to a pharmaceutically acceptable diluent such as water, buffer or saline solution.

For parenteral administration, a compound may be mixed with a suitable carrier or diluent such as water, a oil, saline solution, aqueous dextrose (glucose), and related sugar solutions, and glycols such as propylene glycol or polyethylene glycols. Solutions for parenteral administration contain preferably a water soluble salt of the compound. Stabilizing agents, antioxidizing agents and preservatives may also be added. Suitable antioxidizing agents include sodium bisulfite, sodium sulfite, and ascorbic acid, citric acid and its salts, and sodium EDTA. Suitable preservatives include benzalkonium chloride, methyl- or propyl-paraben, and chlorbutanol.

EXAMPLES

Example 1

Attenuation of Brain Derived Neural Factor Neurotoxicity

Murine corticol subcultures were prepared from fetal mice at 15–16 days gestation. Brains were removed from embryos under sterile conditions and cortices were dissected free and incubated in 0.75% acetylated trypsin at 37° C. for 1 hour. Tissue was then collected by low speed centrifugation and resuspended in Eagles Minimum Essential Medium (MEM) supplemented with 5% Equine Serum, 5% Fetal Bovine Serum, 2 mm glutamine and 23 mm glucose (Plating Medium). Tissue was then dissociated by trituration through a narrow bore flamed Pasteur pipette and diluted in additional Plating Medium. Cells were then plated on confluent glial cultures and 24 well plates at a density 2.5 hemispheres/plate. Cultures were incubated at 5% $CO_2$ at 37° C. Two-thirds of the culture medium was exchanged twice weekly with MEM supplemented with 10% Equine Serum, 2 mm glutamine and 23 mm glucose. Corticoglial cultures were prepared from neonatal Swiss Webster mice using the above technique and plated at a density of 0.5 hemispheres/plate. *Brain Research*, 1995, 682:144–150, incorporated by reference herein in its entirety.

At 12 days in vitro cultures were washed free of serum and exposed to 300 ng/ml BDNF (control) or 300 ng/ml BDNF with 50 μM the piperazine derivative Dexrazoxane (Pharmacia S.p.A., Milan, Italy) for 48 hours. Increased levels of lactate dehydrogenase (LDH) correlates with cell death. LDH study was performed as described in *Brain Research*, 1995, 682:144–150. As shown in FIG. 1, 50 μM of Dexrazoxane resulted in approximately an 80% reduction in cell death. (P<0.05, Dunnett multiple comparisons test).

Example 2

Attenuation of Hemoglobin Neurotoxicity

Figure 2:
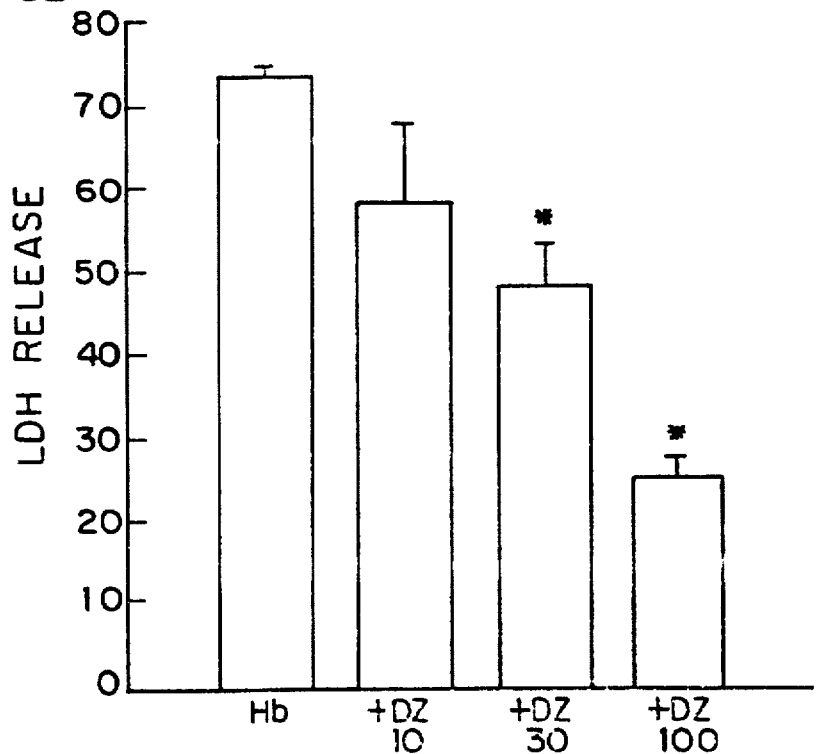
FIG. 2 is a chart showing attenuation of hemoglobin (Hb) neurotoxicity resulting from treatment with 10 μM, 30 μM and 100 μM of Dexrazoxane (DZ).

Cortical cell cultures were prepared from fetal mice as described in Example 1. At 13–15 days in vitro, control cells were exposed to 20 uM hemoglobin alone (control), while other cells were exposed to hemoglobin plus 10 μM, 30 μM and 100 μM concentrations of dexrazoxane. LDH levels was measured by LDH assay at 24 hours which correlates well with cell counts in this system. As shown in FIG. 2, hemoglobin alone (Hb) lysed approximately 75% of the control cells. Dexrazoxane demonstrated a concentration dependent cytoprotective effect with a 50% reduction in cell lysis at concentration of 30 μM. (P<0.01 Dunnett Multiple Comparisons Test). At higher concentrations (300 uM) cell death was exacerbated (results not shown).

What is claimed is:

1. A method of treating acute nervous central nervous system injury in a human comprising:
   identifying a patient suffering from an acute central nervous system injury, and
   administering an effective amount of at least one bisdioxopiperazine.

2. The method of claim 1 wherein a bisdioxopiperazine is (+)-1,2-bis(3,5-dioxopiperazinyl-1-yl) propane.

3. A method of treating free radical injury to neurons in a human comprising:
   identifying a patient suffering from a condition associated with free radical induced injury to neurons of said patient, and
   administering an effective amount of at least one bisdioxopiperazine to said patient.

4. The method of claim 3 wherein free radical induced injury is caused by hemorrhaging into of one or more parts of the central nervous system.

5. A method of preventing free radical injury to neurons in a human comprising:
   identifying a patient at risk of free radical induced injury to neurons of said patient, and
   administering an effective amount of at least one bisdioxopiperazine to said patient.

* * * * *